US008138378B2

(12) United States Patent
Grigsby, Jr. et al.

(10) Patent No.: US 8,138,378 B2
(45) Date of Patent: Mar. 20, 2012

(54) REACTIVE AMINE CATALYSTS FOR POLYURETHANE FOAM

(75) Inventors: Robert A. Grigsby, Jr., Spring, TX (US); Robert L. Zimmerman, Austin, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 223 days.

(21) Appl. No.: 12/663,879

(22) PCT Filed: Jun. 11, 2008

(86) PCT No.: PCT/US2008/066488
§ 371 (c)(1),
(2), (4) Date: Dec. 10, 2009

(87) PCT Pub. No.: WO2008/157151
PCT Pub. Date: Dec. 24, 2008

(65) Prior Publication Data
US 2010/0130715 A1    May 27, 2010

Related U.S. Application Data

(60) Provisional application No. 60/936,303, filed on Jun. 19, 2007.

(51) Int. Cl.
*C07C 209/86*    (2006.01)
*C07C 217/46*    (2006.01)
(52) U.S. Cl. .................. 564/498; 564/499; 564/508
(58) Field of Classification Search .................. 564/498, 564/499
See application file for complete search history.

(56) References Cited

U.S. PATENT DOCUMENTS

| 1,898,461 | A | * | 2/1933 | Nicodemus et al. | .......... 564/499 |
|---|---|---|---|---|---|
| 2,683,730 | A | | 7/1954 | Seeger et al. | |
| 2,950,263 | A | | 8/1960 | Abbotson et al. | |
| 3,012,008 | A | | 12/1961 | Lister | |
| 3,194,773 | A | | 7/1965 | Hostettler | |
| 3,297,597 | A | | 1/1967 | Edwards et al. | |
| 3,344,162 | A | | 9/1967 | Rowton | |
| 3,362,979 | A | | 1/1968 | Bentley | |
| 4,174,351 | A | * | 11/1979 | Shoffner | ........................ 564/425 |
| 4,306,068 | A | * | 12/1981 | Smith, Jr. | ....................... 546/184 |
| 5,225,597 | A | * | 7/1993 | Kurek | ............................. 564/446 |
| 5,481,037 | A | * | 1/1996 | Fuchs et al. | .................... 564/437 |
| 6,011,156 | A | * | 1/2000 | Matson | ........................ 546/184 |
| 6,353,138 | B1 | * | 3/2002 | Rooney | ........................ 564/497 |

OTHER PUBLICATIONS

Stork, Gilbert, et al. "The Enamine Alkylation and Acylation of Carbonyl Compounds", J. Am. Chem. Soc. 85, 207-222 (1963).

* cited by examiner

*Primary Examiner* — Brian J Davis
(74) *Attorney, Agent, or Firm* — Robert A. Diaz

(57) ABSTRACT

A process for the separation of a first amine having a tertiary amine group and a secondary amine group such as N,N,N'-trimethylbis(aminoethyl)ether from a di-tertiary amine such as N,N,N',N'-tetramethylbis(aminoethyl)ether, comprising: contacting a mixture of the first amine and the di-tertiary amine with a carbonyl compound capable of forming an enamine such that the carbonyl compound reacts with the first amine to form an enamine; separating the enamine from the di-tertiary amine; and subsequently converting the enamine to the first amine.

18 Claims, No Drawings

REACTIVE AMINE CATALYSTS FOR POLYURETHANE FOAM

CROSS-REFERENCE TO RELATED APPLICATIONS

This application is the National Phase of International Application PCT/US2008/066488 filed Jun. 11, 2008 which designated the U.S. and which claims priority to U.S. Provisional App. Ser. No. 60/936,303 filed Jun. 19, 2007. The noted applications are incorporated herein by reference.

BACKGROUND OF THE INVENTION

This invention generally pertains to the field of urethane catalysts. More particularly, this invention relates to the purification of amine catalysts that incorporate a reactive hydrogen group.

Amines (mono and poly) are a typical type of catalyst used for making polyurethanes. For example, amines such as N,N,N'-trimethylbis(aminoethyl)ether are useful as a polyurethane catalyst or as a chemical intermediate. When trimethylbis(aminoethyl)ether is prepared N,N,N',N',-tetramethylbis(aminoethyl)ether is also made. Fractional distillation does not separate the trimethyl and tetramethyl compounds. The inventors have recognized that a need exists for a purification method of amines such as N,N,N'-trimethylbis(aminoethyl)ether to remove undesirable coproducts such as N,N,N',N',-tetramethylbis(aminoethyl)ether.

SUMMARY OF THE INVENTION

This invention provides a solution to one or more of the omissions or disadvantages discussed above.

The process of this invention enables the purification of diamines with both tertiary and secondary amine groups such as N,N,N'-trimethylbis(aminoethyl)ether by removing di-tertiary amine compounds of similar structure and molecular weight such as N,N,N',N',-tetramethylbis(aminoethyl)ether co-products.

In one broad respect, this invention is process for the separation of a first amine having a tertiary amine group and a secondary amine group from a di-tertiary amine, by contacting a mixture of the first amine and the di-tertiary amine with a carbonyl compound capable of forming an enamine such that the carbonyl compound reacts with the first amine to form an enamine; separating the enamine from the di-tertiary amine; and subsequently converting the enamine to the first amine. This process may further comprise using the separated first amine as a catalyst to manufacture polyurethane, including the use of the separated first amine as a catalyst to form a polyurethane foam.

The ratio of the tetramethyl product to the trimethyl product can be controlled by those skilled in the process. High levels of the tetramethyl product (99.9%) can be made with very low levels of the trimethyl derivative. Also low levels of the tetramethyl derivative (0.5%) can be made with high levels of the trimethyl derivative (99.5%). In one embodiment, 5-25% of the tetramethyl derivative will be in the product.

In this process the first amine can be of formula A:

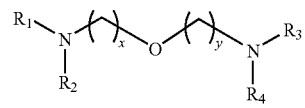

where $R_1$ is alkyl or an alkylene alcohol of from 1 to 6 carbons, especially $CH_3$, $CH_2CH_3$, or $CH_2CH_2OH$; $R_2$ is alkyl or an alkylene alcohol of from 1 to 6 carbons, especially $CH_3$, $CH_2CH_3$, or $—CH_2CH_2OH$; $R_3$ is alkyl or alkylene alcohol of from 1 to 6 carbons, especially $CH_3$, $CH_2CH_3$, or $CH_2CH_2OH$; $R_4$ is hydrogen; x is an integer between 2 and 5; and y is an integer between 2 and 5, and wherein the second amine is of formula A except that R4 is alkyl or an alkylene alcohol. The di-tertiary amine may also be of formula A, except that $R_4$ is alkyl or an alkylene alcohol of from 1 to 6 carbons, especially $CH_3$, $CH_2CH_3$, or $CH_2CH_2OH$. An illustrative first amine of formula A of this invention includes but is not limited to N,N,N'-trimethylbis(aminoethyl)ether.

The first amines of this invention function, for example, as polyurethane catalysts in the reaction between an isocyanate functionality and an active hydrogen-containing compound, i.e. an alcohol, a polyol, an amine or water.

In another broad respect, this invention is a N,N,N'-trialkylbis(aminoethyl)ether-enamine such as N,N,N'-trimethylbis(aminoethyl)ether-enamine, such as formed from N,N,N'-trimethylbis(aminoethyl)ether and cyclohexanone.

Advantageously, this invention provides a process for separating N,N,N'-trimethylbis(aminoethyl)ether from N,N,N',N'-tetramethylbis(aminoethyl)ether, which is not possible through fractional distillation.

DETAILED DESCRIPTION OF THE INVENTION

The first amines used in the practice of this invention include a variety of amines having both tertiary and secondary amine groups. These amines typically contain from 2 to 20 carbon atoms. The first amines may also contain additional functional groups, such as ether groups. One class of first amines that can be used in the practice of this invention are trialkylbis(aminoalkyl)ethers where each alkyl group is separately in each occurrence from 1 to 6 carbons. The first amines can be of formula A, as described herein. A representative example of such a first amine is trimethylbis(aminoethyl)ether.

The di-tertiary amines that are separated from the first amines in the practice of this invention typically contain from 2 to 20 carbons. The di-tertiary amines are typically co-products formed in the production of the first amine. One class of di-tertiary amines used in this invention are tetraalkylbis(aminoalkyl)ethers where each alkyl group is separately in each occurrence from 1 to 6 carbons. The di-tertiary amines can be of formula A as described herein, where each R group is other than hydrogen. A representative example of such a first amine is tetramethylbis(aminoethyl)ether.

In the process of this invention, a mixture of amine and di-tertiary amine is contacted with a carbonyl compound so that the carboxyl containing compound reacts to form an enamines. This contacting can occur at room temperature up to 200 degrees Centigrade, and at a variety of pressures. The formation of enamines is well known in organic chemistry Szmuszkovicz, *Advan. Org, Chem.* 4, 1-113 (1963), pp 9-12. Enamines are often used for the Stork enamine reaction (Stork et. al. *J. Am. Chem. Soc.* 85, 207 (1963). In general, enamine reactions entail reaction of a secondary amine with a carbonyl containing compound that is capable of forming an enamine, such as various ketones and aldehydes. Such ketones and aldehydes are typically aliphatic compounds that typically contain from 2 to 20 carbons, and may be straight chain, branched, or cyclic. Representative examples of such aldehydes and ketones include but are not limited to cyclohexanone. Examples of other ketones include acetone, methylethyl ketone, methyl n-propyl ketone, 3-pentanone, methyl isopropylketone and the like. Examples of aldehydes include acetaldehyde, propionaldehyde, benzaldehyde, p-tolualdehyde, salicyaldehyde, and the like. Typically, a stoichiometric amount of carbonyl compound is used, or excess carbonyl compound is used. Since the di-tertiary amine does not have a secondary amine group, it does not react to form an enamine. Water is produced in the production of the enamines, which must be removed by distillation, azeotrope, or drying agent. It is best to remove the water by azeotrope distillation. Removing the water will drive the reaction toward the enamine. Typical azeotrope agents that can drive the reaction forward with heat and remove water would include diverse agents such as isomers of xylene, which boils in the neighborhood of 138-144 C, or toluene, which boils at 110 C, cyclic alkanes such as cyclohexane, straight chain compounds such as nonene, and the like.

After the enamine is formed, the enamine can be separated from the di-tertiary amine using a variety of procedures. For example, the reaction mixture can be distilled to remove the lighter di-tertiary amine, at temperatures from room temperature to 200 degrees Centigrade, and atmospheric pressure or subatmospheric. Distillation can be accomplished using conventional techniques, and the temperature at which the distillation occurs will vary depending on the first amines and di-tertiary amine, as would be apparent to one of skill in the art. Alternatively, the enamine and di-tertiary amine can be separated using chromatography or other conventional technique. It should be appreciated that small portions of the co-product may remain after the distillation. However, at least a portion of the di-tertiary amine is separated from the first amine. Typically, at least 50 percent by weight of the di-tertiary amine is separated from the first amine, more typically at least 75 percent, and even more typically at least 95 percent.

After the di-tertiary amine has been separated from the enamine, the enamine can be hydrolyzed to reform the first amine by adding water using conventional procedures. The hydrolysis may be conducted at room temperature or with heating up to 200 degrees Centigrade to effect the hydrolysis if needed as would be apparent to one of skill in the art. The first amine can be further purified to remove the ketone, aldehyde, and any other impurities using common techniques such as distillation, chromatography, and so forth. In one embodiment, the mixture is heated during hydrolysis to distill off the carbonyl compound that is reformed by hydrolysis of the enamine, with such elevated temperatures and conditions varying depending on the reactants.

A representative example of a procedure that can be used in the practice of this invention entails providing a mixture of N,N,N'-trimethylbis(aminoethyl)ether and N,N,N'N'-tetramethylbis(aminoethyl)ether which is reacted with a carbonyl compound capable of forming an enamine with the N,N,N'-trimethylbis(aminoethyl)ether. The resulting reaction mixture is distilled to remove the N,N,N'N'-tetramethylbis(aminoethyl)ether and any azeotroping agent, leaving the N,N,N'-trimethylbis(aminoethyl)ether—enamine in the distillation pot. Alternately the enamine could also be distilled. The enamine is then hydrolyzed by adding water and removing the carbonyl compound. This can be performed by, for example, azeotroping the carbonyl of by extraction. N,N,N'-trimethylbis(aminoethyl)ether free of N,N,N'N'-tetramethylbis(aminoethyl)ether can then be obtained by distillation.

The purified first amine can be used as a catalyst to form polyurethane. The production of polyurethane is well known. Polyurethane as used herein refers to polyurethane and/or polyisocyanurate as is understood in the art. The polyurethane prepared from the first amines of this invention include polyurethane foam. Such foams may be formed by incorporation of blowing agents such as those commonly used in the art. Such blowing agents include but are not limited to hydrochlorofulorocarbons, hydrofluorocarbons, chlorofluorocarbons, pentanes, nitrogen, air, carbon dioxide, and so on. The polyurethanes can include water to help create a foam. If used, the amount of water is typically about 0.1 to about 7 parts per hundred parts of polyol.

To prepare polyurethanes using the catalysts of this invention, any suitable organic polyisocyanate may be used. Typical polyisocyanates include but are not limited to m-phenylene diisocyanate, p-phenylene diisocyanate, polymethylene polyphenylisocyanate, 2,4-toluene diisocyanate, 2,6-toluene diisocyanate, dianisidine diisocyanate, bitollene diisocyanate, napthalene-1,4-diisocyanate, xylylene-1,4-diisocyanate, xylylene-1,3-diisocyanate, bis(4-isocyanatophenyl)methane, bis(3-methyl-4-isocyanatophenyl)methane, and 4,4'-diphenylpropane diisocyanate.

In one embodiment, the polyisocyanates used in the practice of the invention include but are not limited to 2,4- and 2,6-toluene diisocyanate (TDI) and methylene-bridged polyphenyl polyisocyanate (MDI) mixtures which have a functionality of from about 2 to 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrocloric acid and/or other acidic catalysts. Known processes for preparing polyamines and corresponding methylene-bridged polyphenyl polyisocyanates therefrom are described in the literature and many patents, for example, U.S. Pat. Nos. 2,683,730; 2,950,263; 3,012,008; 3,344,162; and 3,362,979, incorporated herein by reference.

In one embodiment, methylene-bridged polyphenyl polyisocyanate mixtures used here contain about 20 to about 100 weight percent methylene diphenyl diisocyanate isomers, with the remainder being polymethylene polyphenyl polyisocyanates having higher functionalities and higher molecular weights. Typical of these are the polyphenyl polyisocyanate mixtures containing about 20 to 100 weight percent methylene diphenyl diisocyanate isomers, of which 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979, incorporated herein by reference.

The hydroxyl-containing polyol component which reacts with the isocyanate may suitably be a polyester polyol or a polyether polyol. In one embodiment, the polyol has a hydroxyl number ranging from about 700 to about 25, or lower. When it is desired to provide a flexible foam, the hydroxyl number is preferably in the range from about 25 to 60. For viscoelastic foams, a mixture of polyols and low molecular weight crosslinkers is used. For rigid foams, the hydroxyl number is preferably in the range from 350 to 700. Semi-rigid foams of a desired flexibility are provided when the hydroxyl number is intermediate to the ranges just given. Also for a flexible urethane foam, the polyol can have an average functionality of from about 2 to about 4 and a molecular weight of from about 2,000 to about 6,000. For rigid foams, the functionality of the polyol component is typically from about 4 to about 8.

When the polyol is a polyester, in one embodiment the polyester is a resin having a relatively high hydroxyl value and a relatively low acid value made from the reaction of a polycarboxylic acid with a polyhydric alcohol. The acid component of the polyester is preferably of the dibasic or polybasic type and is usually free of reactive unsaturation, such as ethylenic groups or acetylenic groups. The unsaturation, such as occurs in the rings of such aromatic acids as phthalic acid, terephthalic acid, isophthalic acid, or the like, is non-ethylenic and non-reactive. Thus, aromatic acids may be employed for the acid component. Aliphatic acids, such as succinic acid, adipic acid, sebacic acid, and azelaic acid, may also be employed. In one embodiment, the alcohol component for the polyester contains a plurality of hydroxyl groups and may be for example an aliphatic alcohol, such as ethylene glycol, glycerol, pentaerthritol, trimethylolethane, trimethylolpropane, mannitol, sorbitol, or methyl glycoside. Mixtures of two or more of the above identified alcohols may be employed also if desired.

When the hydroxyl-containing component is a polyether polyol for use in flexible polyurethane foam, the polyol may be for example an alkylene oxide adduct of a polyhydric alcohol with a functionality of about 2 to 4. The alkylene oxide may be for example ethylene oxide, propylene oxide, or 1,2-butylene oxide, or a mixture of some or all of these. The polyol will suitably have a molecular weight within the range from about 2,000 to about 7,000. For flexible polyether polyurethane foams, the alkylene oxide is preferably propylene oxide or a mixture of propylene oxide and ethylene oxide.

For rigid polyether polyurethane foams, the polyol typically has a functionality of from about 3 to about 8 and a molecular weight of from about 300 to about 1,200. Polyols for rigid polyether polyurethane foams may be made in various ways including the addition of an alkylene oxide as above to a polyhydric alcohol with a functionality of from about 3 to 8. These polyols may also be, for example, Mannich condensation products of a phenol, an alkanolamine, and formaldehyde, which Mannich condensation product is then reacted with an alkylene oxide (see U.S. Pat. No. 3,297,597, incorporated herein by reference).

In addition to the polyether and polyester polyols, polymer or graft polyols may also be useful in the process of this invention. There are several types of polymer polyols. Generally the term graft polyol is used to describe a trio in which vinyl monomers are graft copolymerized. Styrene and acrylonitrile are the usual monomers of choice. Another type of polymer polyol referred to as polyurea modified polyol is a polyol containing a polyurea dispersion formed by the reaction of a diamine and TDI. A variant of this type of polymer polyol, called PIPA polyol, is formed by the in-situ polymerization of TDI and alkanolamine in the polyol.

The amount of hydroxyl-containing polyol compound to be used relative to the isocyanate compound in both polyester and polyether foams normally should be such that the isocyanate groups are present in at least an equivalent amount, and preferably, in slight excess, compared to the free hydroxyl groups. Preferably, the ingredients will be proportioned so as to provide from about 0.9 to about 1.5 mole equivalents of isocyanate groups per mole equivalent of hydroxyl groups. However, for certain foams we have found that using the catalyst of our invention the mole equivalents of isocyanate to hydroxyl groups can be as low as 0.4.

When water is used, the amount of water, based on the hydroxyl compound, is suitably within the range of about 0.05 mole to about 10.0 moles per mole equivalent of hydroxy compound.

It is within the scope of the present invention to utilize a blowing agent such as a gas or a gas-producing material. Generally, these blowing agents are inert. For example, halogenated low-boiling hydrocarbons, such as trichloromonofluoromethane and methylene chloride, carbon dioxide, nitrogen, etc. may be used. The inert blowing agent reduces the amount of excess isocyanate and water that is required in preparing flexible urethane foam. For a rigid foam, the use of water is often avoided and the extraneous blowing agent is used exclusively. Selection of the proper blowing agent is well within the knowledge of those skilled in the art. See for example U.S. Pat. No. 3,072,082, incorporated herein by reference.

The catalysts of this invention are useful in the preparation of polyurethane foams, based on the combined weight of the hydroxyl-containing compound and polyisocyanates, are employed in an amount of from about 0.03 to about 10.0 weight percent. More often, the amount of catalyst used is 0.06 to about 2.0 weight percent.

The first amine catalysts of this invention may be used either alone or in a mixture with one or more other catalysts such as tertiary amines or with an organic tin compound or other polyurethane catalysts. The organic tin compound, particularly useful in making flexible foams may suitably be a stannous or stannic compound, such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylhexyltin oxide, dioctyltin dioxide, stannous octoate, stannous oleate, etc. or a mixture thereof, may be used. Such tertiary amines include trialkylamines (e.g., trimethylamine, triethylamine), heterocyclic amines such as N-alkylmorpholines (e.g., N-methylmorpholine, N-ethylmorpholine, etc.), 1,4-dimethylpiperazine, triethylenediamine, etc., and aliphatic polyamines, such as N,N,N',N'-tetramethyl-1,3-butanediamine.

Conventional formulation ingredients are also employed, such as, for example, foam stabilizers, also known as silicon oils or emulsifiers. The foam stabilizer may be an organic silane or siloxane. For example, compounds may be used having the formula:

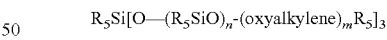

$R_5Si[O—(R_5SiO)_n\text{-(oxyalkylene)}_mR_5]_3$ wherein $R_5$ is independently in each occurrence an alkyl or alkylene group containing from 1 to 4 carbon atoms; n is an integer of from 4 to 8; m is an integer from 20 to 40; and the oxyalkylene groups are derived from propylene oxide and ethylene oxide. See, for example, U.S. Pat. No. 3,194,773, incorporated herein by reference.

Other conventional additives and auxiliary agents that can be employed include cell regulators, crosslinkers, flame retardants, plasticizers, fillers, pigments, among others.

In preparing a flexible foam, the ingredients may be simultaneously, intimately mixed with each other by the so-called "one-shot" method to provide a foam by a one-step process. In this instance, water should comprise at least a part (e.g. 10% to 100%) of the blowing agent. The foregoing methods are known to those skilled in the art, as evidenced by the following publication: duPont Foam Bulletin, "Evaluation of Some Polyols in One-Shot Resilient Foams", Mar. 22, 1960.

When it is desired to prepare rigid foams, the "one-shot" method or the so-called "quasi-prepolymer method" is employed, wherein the hydroxyl-containing component preferably contains from about 4 to 8 reactive hydroxyl groups, on the average, per molecule.

In accordance with the "quasi-prepolymer method", a portion of the hydroxyl-containing component is reacted in the absence of a catalyst with the polyisocyanate component in proportions so as to provide about 20 percent to about 40 percent of free isocyanato groups in the reaction product, based on the polyol. To prepare a foam, the remaining portion of the polyol is added and the two components are allowed to react in the presence of catalytic systems such as those discussed above and other appropriate additives, such as blowing agents, foam stabilizing agents, fire retardants, etc. The blowing agent (e.g. a halogenated lower aliphatic hydrocarbon), the foam-stabilizing agent, the fire retardant, etc., may be added to either the prepolymer or remaining polyol, or both, prior to the mixing of the component, whereby at the end of the reaction a rigid polyurethane foam is provided.

Urethane elastomers and coatings may be prepared also by known techniques in accordance with the present invention wherein the catalyst of this invention is used.

The invention will be illustrated further with respect to the following specific examples, which are given by way of illustration and not as limitations on the scope of this invention.

1. Preparation of Enamine.

To a 1-liter flask equipped with a Dean-Stark trap was place 245.5 grams of a mixture of N,N,N'-trimethylbis(aminoethyl) ether and N,N,N'N'-tetramethylbis(aminoethyl)ether (81.5% tri, 16.9% tetra and 1.6% di), 160 grams of cyclohexanone and 81 grams of xylene. The mixture was heated to reflux and the water removed by an azeotrope using the Dean-Stark trap. Once all the water had been remove the flask was equipped with a 6-inch Vigreux column and the reaction mixture distilled first at atmospheric pressure to a head temperature of 155 C then under 10 mM Hg vacuum to a head temperature of 90 C to thereby remove the tetramethyl compound.

2. Hydrolysis of Enamine

To a 500 ml flask equipped with an azeotroping head which returns the heavy layer water layer to the reaction flask and allows for the removal of the light organic layer was charged 120.4 grams of the bottoms from the previous reaction and 120 grams of water. The mixture was heated to reflux removing the cyclohexanone by hydrolysis of the enamine by the azeotrope formed with water then remove the water.

3. Isolation of Pure N,N,N'-trimethylbis(aminoethyl)ether

To a distillation flask equipped with a 6-inch Vigreux distillation column was placed 233.2 grams of the crude reaction product from example 2 and 100 grams of diethylene glycol and distilled at 20 mm Hg vacuum. The gas chromatogram of the product cut showed 98.4 A % N,N,N'-trimethylbis(aminoethyl)ether with no N,N,N'N'-tetramethylbis(aminoethyl) ether being detected.

4. Comparison Example Showing Distillation does not Separate the Trimenthyl and Tertamethyl Compounds.

To a distillation flask equipped with a 36-inch distillation column, packed with Goodloe packing material, was place 279.19 grams of the mixed N,N,N',N'-tetramethylbis(aminoethyl)ether (17.0%) and N,N,N'-trimethylbis(aminoethyl) ether (81.3%) mixed material. The distillation flask was heated to 77 C under 7 mm of vacuum. Using a reflux rate of 15 to 2, only one cut was taken since there was no change in head temperature, 66 C. This cut, 152.09 grams had a composition of 84.5% N,N,N'-trimethylbis(aminoethyl)ether and 14.2% N,N,N',N'-tetramethylbis(aminoethyl)ether.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A process for the separation of a first amine having a tertiary amine group and a secondary amine group from a di-tertiary amine, comprising: contacting a mixture of the first amine and the di-tertiary amine with a carbonyl compound capable of forming an enamine such that the carbonyl compound reacts with the first amine to form an enamine; separating the enamine from the di-tertiary amine; and subsequently converting the enamine to the first amine.

2. The process of claim 1, wherein the first amine is of formula A:

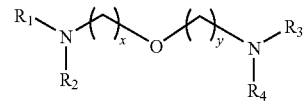

where $R_1$ is alkyl or an alkylene alcohol of from 1 to 6 carbons; $R_2$ is alkyl or an alkylene alcohol of from 1 to 6 carbons; $R_3$ is alkyl or alkylene alcohol of from 1 to 6 carbons; $R_4$ is hydrogen; x is an integer between 2 and 5; and y is an integer between 2 and 5.

3. The process of claim 2, wherein $R_1$ is $CH_3$, $CH_2CH_3$, or $CH_2CH_2OH$.

4. The process of claim 2, wherein $R_2$ is $CH_3$, $CH_2CH_3$, or $CH_2CH_2OH$.

5. The process of claim 2, wherein $R_3$ is $CH_3$ or $CH_2CH_3$.

6. The process of claim 1, wherein $R_1$ is $CH_3$, $CH_2CH_3$, or $CH_2CH_2OH$; $R_2$ is $CH_3$, $CH_2CH_3$, or $CH_2CH_2OH$; and $R_3$ is $CH_3$ or $CH_2CH_3$.

7. The process of claim 2, wherein the first amine is N,N,N'-trimethylbis(aminoethyl)ether and the di-tertiary amine is N,N,N',N'-tetramethylbis(aminoethyl)ether.

8. The process of claim 1, where the enamine is converted by hydrolysis.

9. The process of claim 1, wherein the carbonyl compound is a ketone or aldehyde.

10. The process of claim 1, wherein the carbonyl compound is a ketone or aldehyde having 2 to 20 carbons.

11. The process of claim 1, wherein the carbonyl compound is cyclohexanone.

12. The process of claim 1, wherein the di-tertiary amine is of formula A:

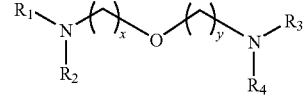

where $R_1$ is alkyl or an alkylene alcohol of from 1 to 6 carbons; $R_2$ is alkyl or an alkylene alcohol of from 1 to 6 carbons; $R_3$ is alkyl or alkylene alcohol of from 1 to 6 carbons; $R_4$ is alkyl or an alkylene alcohol of from 1 to 6 carbons; x is an integer between 2 and 5; and y is an integer between 2 and 5.

13. The process of claim 1, wherein during the contacting, water is removed as the enamine is formed.

14. The process of claim 1, wherein the enamine is separated from the di-tertiary amine by distillation.

15. The process of claim 1, further comprising removing the reformed carbonyl compound after converting the enamine to the first amine.

16. A process for the separation of N,N,N'-trimethylbis(aminoethyl)ether from N,N,N',N'-tetramethylbis(aminoethyl)ether, comprising: contacting a mixture of the N,N,N'-trimethylbis(aminoethyl)ether and N,N,N',N'-tetramethylbis(aminoethyl)ether with a carbonyl compound capable of forming an enamine such that the carbonyl compound reacts with the N,N,N'-trimethylbis(aminoethyl)ether to form an enamine; separating the enamine from the N,N,N',N'-tetramethylbis(aminoethyl)ether; and subsequently converting the enamine to reform the N,N,N'-trimethylbis(aminoethyl)ether.

17. A N,N,N'-trialkylbis(aminoethyl)ether-enamine.

18. The enamine of claim 17, wherein the enamine is formed from N,N,N'-trimethylbis(aminoethyl)ether and cyclohexanone.

* * * * *